(12) United States Patent
Dreyer

(10) Patent No.: US 6,576,808 B1
(45) Date of Patent: Jun. 10, 2003

(54) APPARATUS AND METHOD TO PROTECT AN IMPLANTED MEDICAL DEVICE OR WOUND

(76) Inventor: Norma S. Dreyer, 221 E. 24th Pl., Tulsa, OK (US) 74114

( * ) Notice: Subject to any disclaimer, the term of this patent is extended or adjusted under 35 U.S.C. 154(b) by 0 days.

(21) Appl. No.: 09/795,377

(22) Filed: Feb. 26, 2001

(51) Int. Cl.[7] .......................... A61F 13/00; B60R 22/00
(52) U.S. Cl. ......................... 602/42; 602/60; 297/482; 280/808; 128/112.1; 128/117.1; 128/120.1
(58) Field of Search ................ 602/41–59, 19.3, 602/20, 21, 23, 26, 60, 61, 62, 63, 64; 128/888, 809, 892, 890, 893, 894, 96.1, 98.1, 99.1, 112.1; 604/380, 304, 174, 179, 180; 297/464, 461, 482, 483, 484, 487, 488; 280/748, 751, 801, 808; D2/639; D11/200

(56) References Cited

U.S. PATENT DOCUMENTS

| | | | |
|---|---|---|---|
| 2,663,020 A | * 12/1953 | Cushman | |
| 3,397,913 A | 8/1968 | Fein | 297/385 |
| 3,782,378 A | * 1/1974 | Page | |
| 3,936,075 A | 2/1976 | Jelliffe | 280/150 B |
| 3,941,404 A | 3/1976 | Otaegui-Ugarte | 280/150 AB |
| 4,466,428 A | * 8/1984 | McCoy | 602/26 |
| 4,595,618 A | 6/1986 | Caringer | 428/100 |
| 4,610,463 A | 9/1986 | Efrom | 280/751 |
| 4,678,205 A | 7/1987 | Wold | 280/808 |
| D301,084 S | 5/1989 | Mathews | D2/639 |
| 4,921,273 A | 5/1990 | Weightman et al. | 280/808 |
| 4,953,569 A | * 9/1990 | Lonardo | 128/892 |
| 5,364,339 A | * 11/1994 | Carver | 602/47 |
| 5,415,642 A | 5/1995 | Shepherd | 604/344 |
| 5,445,601 A | * 8/1995 | Harlow | |
| 5,620,234 A | 4/1997 | Gunby | 297/482 |
| 5,795,030 A | 8/1998 | Becker | 397/488 |
| 5,911,479 A | 6/1999 | Atkinson | 297/482 |

OTHER PUBLICATIONS

Soft Touch International web–site, www.aboutsofttouch.com, believed to be originally put online on or about Aug. 22, 2001, 15 pages attached.

* cited by examiner

Primary Examiner—Kim M. Lewis
(74) Attorney, Agent, or Firm—Doerner, Saunders, Daniel & Anderson, L.L.P.

(57) ABSTRACT

An apparatus and method for protecting an implanted medical device such as a catheter or ostomy stoma from the force exerted by wearing a seatbelt or other strap by placing an annular shaped structure over the top of the medical device to bridge the seatbelt over the top of the device, thus transferring the force to the area surrounding the device. Alternate embodiments of the apparatus may contain a clip, loop, snap or other fastener to attach the apparatus to the seatbelt or other strap, thus holding the apparatus in place while in use.

16 Claims, 4 Drawing Sheets

APPARATUS AND METHOD TO PROTECT AN IMPLANTED MEDICAL DEVICE OR WOUND

REFERENCE TO PENDING APPLICATIONS

This appliction is not related to any pending applications.

REFERENCE TO MICROFICHE APPENDIX

This appliction is not referenced in any microfiche appendix.

1. Technical Field of the Invention

This invention relates to an apparatus and method to protect an incision, wound, catheter implant, colostomy bag port or other medical device from forces exerted on it by a seatbelt.

2. Background of the Invention

In the practice of modern medicine, it is often necessary and advantageous to implant a catheter. These catheters are typically located on the front of the torso in the upper chest area or lower abdominal area. These catheters are used as an injection port for certain medical treatments, such as chemotherapy or dialysis.

Certain digestive problems require treatment of insertion of feeding tubes through the stomach wall with a catheter extending out through the abdomen. Still other medical treatments require the placement of a colostomy bag port connecting to the intestine of the patient. The port goes through the abdomen wall of the patient.

The treatments mentioned above are all very intrusive in nature. One of the problems the patient faces is the discomfort of wearing a seatbelt. The seatbelt typically crosses over areas of the torso used for these catheters, feeding tubes and colostomy ports. A seatbelt worn across the top of these implanted medical devices can cause discomfort to the patient. This discomfort can lead the patient to discontinue using seatbelts and other related devices. The discontinued use of the seatbelt can lead to problems with insurance coverage in the event an accident occurs and the patient incurs injuries from the accident while not wearing a seatbelt.

Purported improvements to seatbelt and catheter protection devices are known and represented in the prior art. For example:

Design Pat. No. 301,084 issued on May 16, 1989 to Bearl D. Mathews discloses a belt pad.

U.S. Pat. No. 3,397,913 issued on Aug. 20, 1968 to R. A. Fein discloses a detachable decorated seatbelt cover.

U.S. Pat. No. 3,936,075 issued on Feb. 3, 1976 to Robin Steward Jelliffe discloses a device for protecting pregnant women drivers or passengers from injury to the abdomen during sudden or unexpected braking of a moving vehicle. The device in one form is a dome shaped shield of rigid plastics material, which is adapted to fit over the protuberant abdomen.

U.S. Pat. No. 3,941,404 issued on Mar. 2, 1976 to Jose Maria Otaegui-Ugarte discloses a protective breastplate rigidly attached to the straps of a vehicle seatbelt in which fiber reinforced material layers are shaped to form an air-tight, hollow chamber anatomically adapted to the upper thorax and abdomen of a vehicle occupant; a metal mesh lining is provided on the interior of the chamber to prevent pointed objects from piercing the protector, and an air intake valve is attached at the bottom.

U.S. Pat. No. 4,595,618 issued on Jun. 17, 1986 to Ronald L. Caringer discloses an accessory used in combination with a vehicle seatbelt characterized as a novelty item, such as a stuffed teddy bear or the like, secured to a sleeve through which the seatbelt is selectively introduced. The arrangement serves entertainment and, importantly, safety purposes for a child user, with the belt, when secured for use, presenting the novelty item in a displayed and/or lap held position. In another assembly procedure, the sleeve could be slit along its length for placement after the seatbelt is in a use condition.

U.S. Pat. No. 4,610,463 issued on Sep. 9, 1986 to Harriet Efrom discloses a protection assembly generally in the form of a shield used to protect the abdominal area of a pregnant woman especially when seated in a vehicle or like structure. A dome-like shield is specifically configured to overlie and at least partially surround the abdominal area which, in a pregnant woman, is generally distended dependent upon the length of the term of pregnancy. Force directing means are secured to opposite ends of the extremities of the shield-like casing and disposed in abutting relation to supporting surfaces of a seat or like structure on which the user is positioned. The casing is sufficiently spaced from the abdominal area of the user such that when any force is exerted thereon, such as contact with the steering wheel or other interior portions of the car in an emergency situation, such forces are effectively absorbed by the casing and transferred to the seat or like supporting structure and not to the abdominal area or the fetus being carried. The casing is further disposed to engage the user, such as in emergency stops, in a manner which will more evenly distribute any stress or force exerted on the user in an area surrounding the abdominal area rather than directly thereon.

U.S. Pat. No. 4,678,205 issued on Jul. 7, 1987 to Jay S. Wold discloses a covering of comfortable material provided with a means so it can be joined to the safety harness of a vehicle and be readily moved to a position in contact with the user of the safety harness. The covering of comfortable material will automatically move to a storage position when the safety harness is removed and released.

U.S. Pat. No. 4,921,273 issued on May 1, 1990 to Judy M. Weightman and Andrew K. Kirikitani discloses a clean and decorative wraps for automotive shoulder belts. The shoulder belt minicover and cushion wraps around and closes with hook and pile type fastening or closure. The minicover for the shoulder belt may have an intermediate layer of padding material. The particular material ranges widely from strong nylon or denim to quilted cloth, fake fur, real fur or sheepskin. The minicover overlies the shoulder and neck area of a user. Bright and reflective surfaces of minicovers indicate shoulder belt usage. Unique shapes and bright colors remind occupants to use seatbelts.

U.S. Pat. No. 5,415,642 issued on May 16, 1995 to Brad Shepherd discloses a fluid-impermeable protective shield for covering the proximal end of an indwelling, percutaneous catheter and the puncture site through which the catheter extends. A medical grade adhesive is used to attach the protective shield to the skin that surrounds the puncture site. The protective shield allows the patient to swim or bathe without undue risk of infection.

U.S. Pat. No. 5,620,234 issued on Apr. 15, 1997 to Judy W. Gunby discloses a seatbelt cushion that includes a cushion comprising a foam like interior which is permanently encased by a cushion face. In the preferred embodiment, VELCRO™ fastening elements enable the device to be secured to a seatbelt by means a VELCRO™ backing secured to the length of the seatbelt. The seatbelt cushion, therefore, can be attached anywhere along the length of the seatbelt. Once secured, the seatbelt cushion may be slid along the length of the seatbelt in order to adjust to fit an individual of any height, weight, gender or other physical characteristics. The seatbelt cushion is manufactured in a variety of lengths, widths and degrees of thickness to accommodate the demands of the particular user. Moreover, the seatbelt user can be utilized in conjunction with the seatbelts of automobiles, trucks, buses and airplanes. Protracted sides on either distal end of the cushion prevent the entire seatbelt from contacting the user's torso. Further, the face of the cushion padding comprises protruding columns of varying lengths, enabling the seatbelt cushion to function as a messaging means.

U.S. Pat. No. 5,795,030 issued on Aug. 18, 1998 to Karl W. Becker discloses a seatbelt pad with a padded area for abdominal support. There are two basic embodiments one for two-point seatbelts and the other for three-point seatbelts. The two-point belt has an oval shaped pad that has seatbelt fittings on both sides of the pad. The vehicle's seatbelts can then be clipped to the fittings on the pad. In this way, the pad, which is considerably larger than an ordinary seatbelt, protects the user's abdomen. The pad is designed to have equal or greater strength than ordinary seatbelts. The three point-pad has two outer bands that fit over an ordinary three-point seatbelt. The bands have VELCRO™ attaches to close the bands around the seatbelts. A layer of mesh extends between the belts and is used to support the user's abdomen.

U.S. Pat. No. 5,911,479 issued on Jun. 15, 1999 to Robert A. Atkinson discloses a new seatbelt comfort pad for providing comfort to the shoulder of a user of a seatbelt having a shoulder strap. The inventive device includes a base having first and second surfaces, a pair of ends, and a pair of sides. The second surface of the base has a plurality of spaced apart elongate ridges thereon which are extended between the ends of the base. A pair of spaced apart elongate side walls are extended from the first surface of the base to define a channel between them. A cross member is extended between the terminal edges of the side walls. The cross member is spaced apart from the first surface of the base to define an opening therebetween. The cross member is located on the side walls adjacent one of the ends of the base. The cross member preferably has a break through

BRIEF SUMMARY OF THE INVENTION

The invention provides a protective apparatus and method to protect the implanted medical device, incision or wound from forces exerted upon it by the use of a seatbelt. The apparatus encircles the area of the implanted medical device, incision or wound and provides a bridge for the seatbelt to cross over the area above the implanted medical device, incision or wound without causing pressure on that area. It also cushions the surrounding area from the pressure of the seatbelt. The device can be held in place by a number of fastening devices. It can also be held in place by the force exerted on the torso by the seatbelt.

Other objects and further scope of the applicability of the present invention will become apparent from the detailed description to follow, taken in conjunction with the accompanying drawings wherein like parts are designated by like reference numerals.

DETAILED DESCRIPTION OF THE PREFERRED EMBODIMENT

While the making and using of various embodiments of the present invention are discussed in detail below, it should be appreciated that the present invention provides for inventive concepts capable of being embodied in a variety of specific contexts. The specific embodiments discussed herein are merely illustrative of specific manners in which to make and use the invention and are not to be interpreted as limiting the scope of the instant invention.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is clear that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

Figure 1:
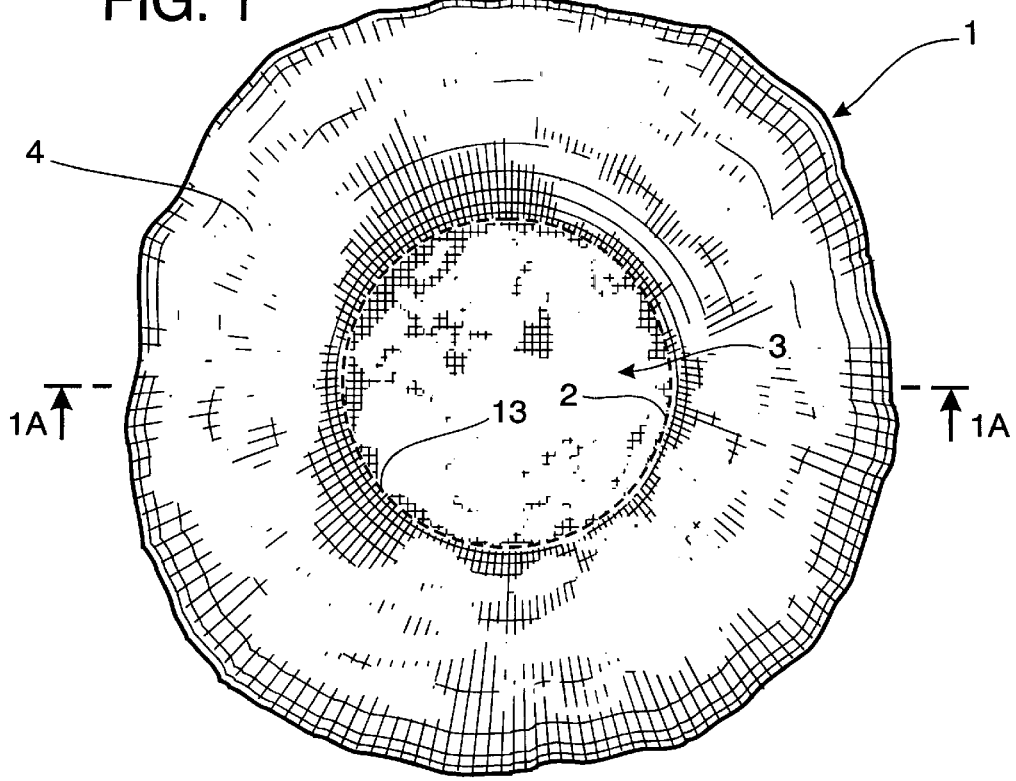
FIG. 1 is a front view of one embodiment of the present invention.

FIG. 1 shows one embodiment of the apparatus of the present invention. The shield 1 is shown in a front view. It is substantially in the geometric shape of an annular ring. The interior wall of the annular ring 2 is indicated. There is a surface 3 which extends across the hole defined by the interior wall of the annular ring 3. The embodiment of the invention as shown in FIG. 1 shows the surface 3 completely filling in the hole formed by the interior wall of the annular ring 2. This embodiment of the present invention is constructed of two pieces of cloth sewn together with an internal seam 13 and an external seam 14. However it could be formed out of many other types of material using many other types of processes including, but not limited to, injection molding of neoprene, foam rubber or a plastic or fusing two sheets of a plastic together at the internal seam 13 and external seam 14 and filling the padded cross section 4 with air or other fluid.

Figure 1A:
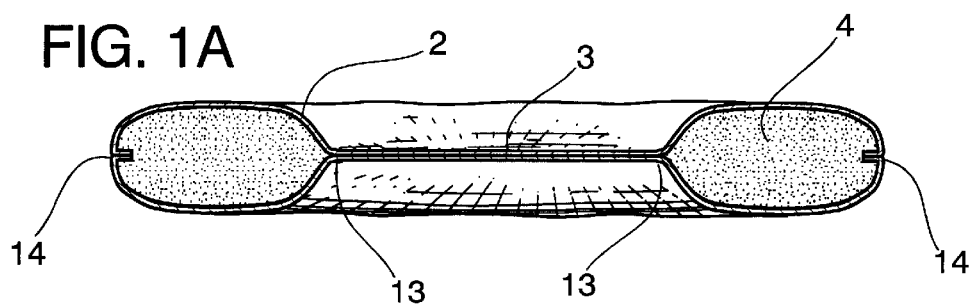
FIG. 1A is a cross section of FIG. 1.

FIG. 1A shows a sectional diagram of the shield 1 shown in FIG. 1. The padded cross section 4 along with the interior wall of the annular ring 2 and the surface 3 are also shown.

Figure 2:
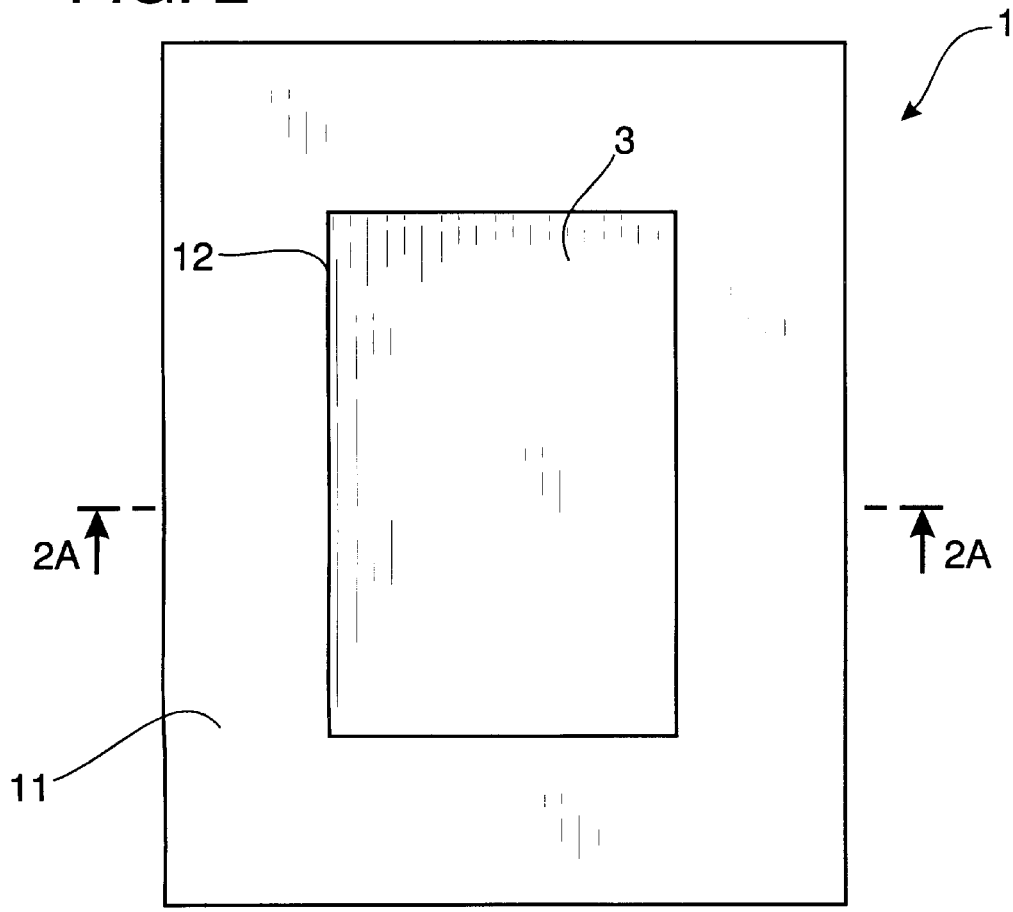
FIG. 2 is a front view of one embodiment of the present invention.
Figure 2A:
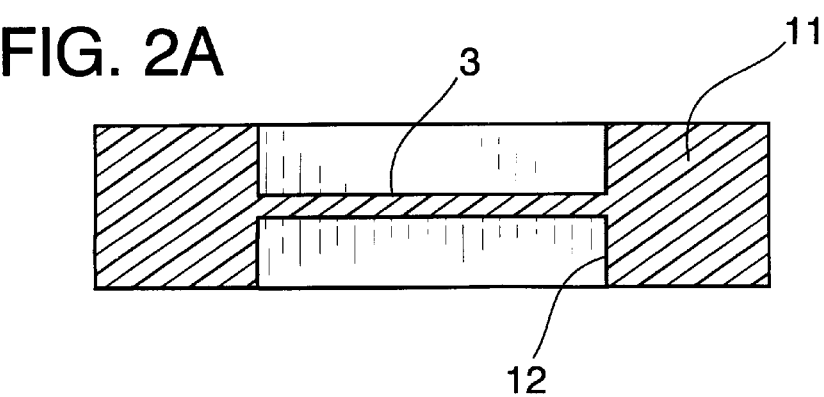
FIG. 2A is a cross section of FIG. 2.

Due to the simplicity of the present invention, it can be adapted to many different geometrical shapes. FIG. 2 shows the present invention in the embodiment of a rectangle. The padded cross section 11 is also in a rectangular shape. The padded cross section interior wall 12 is also marked. The shield 1 could also be adapted to an oval or elliptical shape. The dimensions and size of the present invention can also be adapted to fit the device or wound to be protected.

Figure 3:
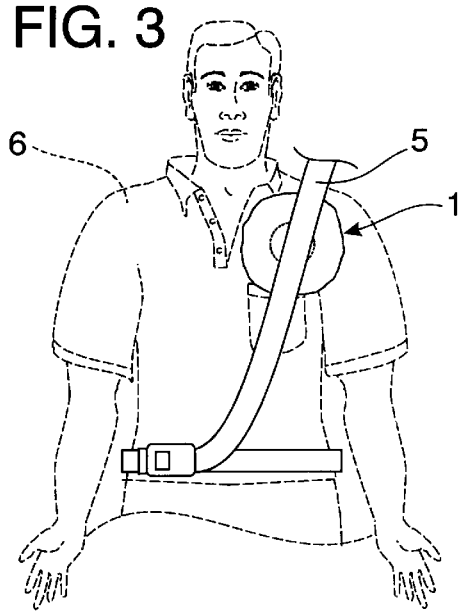
FIG. 3 is a diagram of the present invention in use.

FIG. 3 shows a user 6 wearing a seatbelt 5 with the shield 1 in place on the upper torso.

Figure 4:
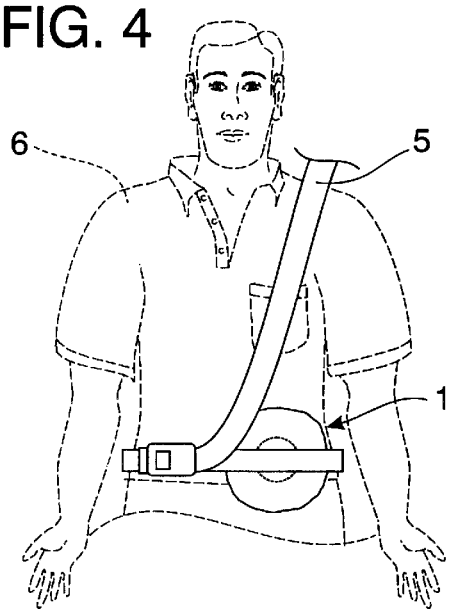
FIG. 4 is a diagram of the present invention in use.

FIG. 4 shows a user 6 wearing a seatbelt 5 with the shield 1 in place on the lower torso. The shield 1 is designed such that it can be placed over an incision, wound, implanted catheter, colostomy bag port, or other implanted medical devices. When in use the incision, wound or implanted medical device resides within the cavity created by the interior wall of the annular ring 2 and on one side of the surface 3. The seatbelt 5 is strapped across the top of the shield 1. The shield 1 bridges the seatbelt 5 across the implanted medical device without applying any force directly on the implanted medical device. The force from the seatbelt 5 is transferred to the area surrounding the implanted medical device and lying directly underneath the padded cross section 4.

Figure 5:
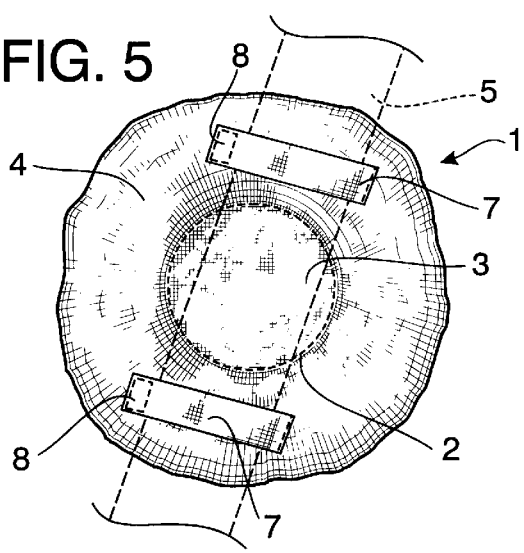
FIG. 5 is one embodiment of the fastening device of the present invention.
Figure 6:
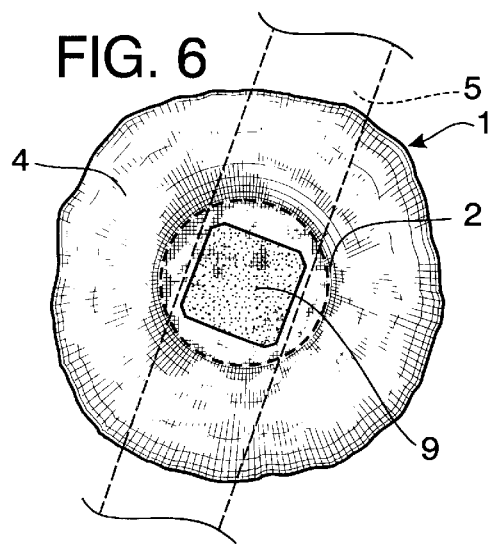
FIG. 6 is another embodiment of the fastening device of the present invention.
Figure 7:
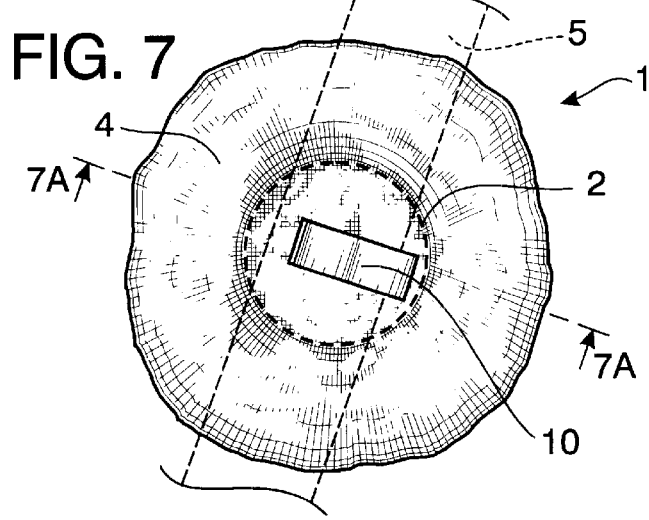
FIG. 7 is a third embodiment of the fastening device of the present invention.
Figure 7A:
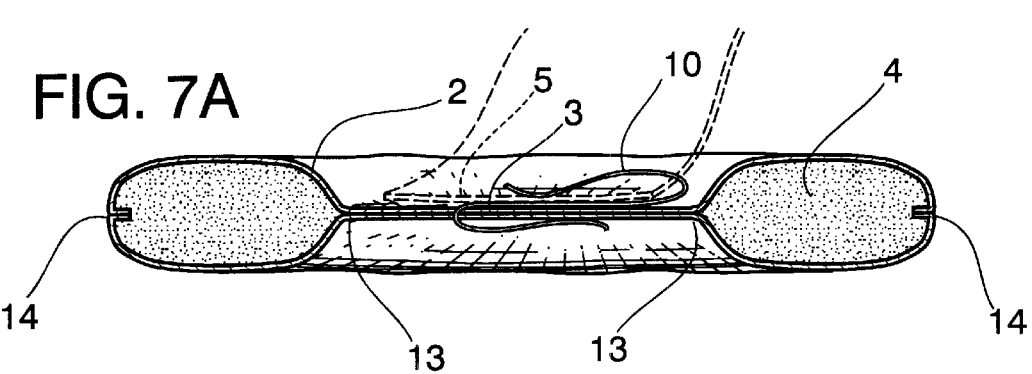
FIG. 7A is a cross section of FIG. 7.

FIGS. 5, 6 and 7 show various embodiments of the fastening device. Due to the basic nature of the present invention, it can be used with numerous fastening devices to hold it in place. FIG. 5 shows the shield 1 in use with a seatbelt 5. The shield 1 is being held in place by two loops 7 located on the padded cross section 4. These loops 7 can open and close by engaging and disengaging the fastener 8. The fastening mechanism 8 could be any one of a number of fastening mechanism including, but not limited to, a snap, a button or a hook and loop adhesive, such as VELCRO™. In addition to locating the loop or loops 7 on the padded cross section 4 of the shield 1, it would also be possible to hold the shield 1 in place by placing the loop or loops 7 on the surface 3.

FIG. 6 shows another embodiment of the present invention. The shield 1 is attached to the seatbelt 5 via a piece of loop and hook adhesive 9. Here again, the loop and hook adhesive 9 could be one or more pieces of loop and hook adhesive and could be located on either the surface 3 or the padded cross section 4.

FIG. 7 shows a third embodiment of the present invention. The shield 1 is held in place on the seatbelt 5 with the use of a clip 10. The clip 10 is mounted on the surface 3. Here again, the shield 1 could be held in place by one or more clips 10 located on either the surface 3 or the padded cross section 4.

It should also be noted that the present invention might be used without a fastening device in which case the shield 1 would be held in place between the seatbelt 5 and the user 6 due to the force exerted on the user 6 by the seatbelt 5.

It should further be noted that if the fastening devices holding the shield 1 in place are located on the padded cross section 4 or if there are no fastening devices used with the shield 1 that it is possible to use the present invention in a configuration where there would not be a surface 3 covering the hole created by the interior wall of the annular ring 2.

While this invention has been described to illustrative embodiments, this description is not to be construed in a limiting sense. Various modifications and combinations of the illustrative embodiments as well as other embodiments will be apparent to those skilled in the art upon referencing this disclosure. It is therefore intended that this disclosure encompass any such modifications or embodiments.

What is claimed is:

1. A shield to protect the site of an implanted medical device from the application of external forces, comprising:

a padded cross section constructed in the shape of a ring with an interior wall;

a cavity defined by the interior wall of the ring; and a hook and loop adhesive with a hook side and a loop side, wherein one of the sides is attached to the shield and the other side is attached to a seatbelt.

2. A shield as claimed in claim 1 where in the cavity is enclosed on one side.

3. The shield as claimed in claim 2, wherein the padded cross section and the surface extending across the interior cavity are fabricated from neoprene.

4. The shield as claimed in claim 1, wherein the padded cross section comprises a bladder of air.

5. A shield as claimed in claim 1 wherein the ring is rectangular.

6. A shield as claimed in claim 1 wherein the ring is elliptical.

7. A shield to protect the site of an implanted medical device from the application of external forces, comprising:

a padded cross section constructed in the shape of a ring with an interior wall;

a cavity defined by the interior wall of the ring; and a clip to hold the shield in place on a seatbelt.

8. A shield as claimed in claim 7 wherein the cavity is enclosed on one side padded cross section comprises a bladder of air.

9. A shield as claimed in claim 8 wherein the padded cross section and the surface extending across the interior cavity are fabricated from neoprene.

10. A shield as claimed in claim 7 wherein the cavity is enclosed on one side padded cross section comprises a bladder of air.

11. A shield as claimed in claim 7 wherein the ring is elliptical.

12. A shield as claimed in claim 7 wherein the ring is rectangular.

13. A method for protecting the site of a catheter from the application of external forces of a seatbelt, comprising:

placing an annular ring shaped structure over the top of the site, bridging the seatbelt over the top of the site, and transferring forces to the area surrounding the site without exerting any force directly on the site.

14. A method for protecting the site of a catheter from the application of external forces of a seatbelt, comprising:

placing a ring shaped structure over the top of the site, bridging the seatbelt over the top of the site, and transferring forces to the area surrounding the site without exerting any force directly on the site.

15. A method for protecting the site of the catheter as claimed in claim 14 wherein the ring shaped structure is rectangular.

16. A method for protecting the site of a catheter is claimed in claim 14 wherein the ring shaped structure is elliptical.

* * * * *